(12) United States Patent
Tran et al.

(10) Patent No.: US 7,749,242 B2
(45) Date of Patent: Jul. 6, 2010

(54) EXPANDING VASO-OCCLUSIVE DEVICE

(75) Inventors: Tri Tran, Fremont, CA (US); Michael P. Wallace, Fremont, CA (US); Brent Gerberding, San Jose, CA (US); Like Que, Union City, CA (US); Jimmy D. Dao, Milpitas, CA (US); Thach Cao, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 76 days.

(21) Appl. No.: 10/873,982

(22) Filed: Jun. 21, 2004

(65) Prior Publication Data

US 2005/0283183 A1 Dec. 22, 2005

(51) Int. Cl.
*A61M 29/00* (2006.01)
(52) U.S. Cl. .................. 606/194; 606/191; 606/200
(58) Field of Classification Search ............ 606/191, 606/194; 600/200; 604/8
See application file for complete search history.

(56) References Cited

U.S. PATENT DOCUMENTS

| | | | |
|---|---|---|---|
| 3,174,851 A | 3/1965 | Buehler | |
| 3,351,463 A | 11/1967 | Rozner | |
| 3,753,700 A | 8/1973 | Harrison et al. | |
| 4,739,768 A | 4/1988 | Engelson | |
| 4,994,069 A | 2/1991 | Ritchart et al. | |
| 5,122,136 A | 6/1992 | Guglielmi et al. | |
| 5,226,911 A | 7/1993 | Chee et al. | |
| 5,304,194 A | 4/1994 | Chee et al. | |
| 5,354,295 A | 10/1994 | Guglielmi et al. | |
| 5,382,259 A | 1/1995 | Phelps et al. | |
| 5,423,849 A * | 6/1995 | Engelson et al. | 606/191 |
| 5,690,666 A | 11/1997 | Berenstein et al. | |
| 5,718,711 A | 2/1998 | Berenstein et al. | |
| 5,826,587 A | 10/1998 | Berenstein et al. | |
| 5,911,731 A * | 6/1999 | Pham et al. | 606/191 |
| 5,935,145 A | 8/1999 | Villar et al. | |
| 5,972,019 A | 10/1999 | Engelson et al. | |
| 5,984,929 A | 11/1999 | Bashiri et al. | |
| 6,156,061 A | 12/2000 | Wallace et al. | |
| 6,165,178 A | 12/2000 | Bashiri et al. | |
| 6,231,586 B1 | 5/2001 | Mariant | |
| 6,280,457 B1 | 8/2001 | Wallace et al. | |

(Continued)

FOREIGN PATENT DOCUMENTS

WO   WO 02/45596 A2   6/2002

(Continued)

OTHER PUBLICATIONS

Barnes Clive, "Shape Memory and Superelastic Alloys", http:llwww.copper.orglinnovations119991071shape.html, Jul. 1999.*

(Continued)

*Primary Examiner*—Melanie J Hand
(74) *Attorney, Agent, or Firm*—Vista IP Law Group LLP

(57) ABSTRACT

This is a device for occluding a space within the body. In particular, the device comprises an expandable member, an inner member and one or more stop elements. The devices may be placed in a desired site within a mammal to facilitate the formation of an occlusion.

18 Claims, 7 Drawing Sheets

U.S. PATENT DOCUMENTS

| | | | |
|---|---|---|---|
| 6,287,318 B1 * | 9/2001 | Villar et al. | 606/191 |
| 6,299,627 B1 * | 10/2001 | Eder et al. | 606/191 |
| 6,312,421 B1 | 11/2001 | Boock | |
| 6,425,914 B1 | 7/2002 | Wallace et al. | |
| 6,458,119 B1 | 10/2002 | Berenstein et al. | |
| 6,533,801 B2 | 3/2003 | Wallace et al. | |
| 6,585,754 B2 | 7/2003 | Wallace et al. | |
| 6,623,493 B2 | 9/2003 | Wallace et al. | |
| 2002/0143362 A1 * | 10/2002 | Macoviak et al. | 606/200 |
| 2003/0195553 A1 * | 10/2003 | Wallace et al. | 606/200 |
| 2004/0193178 A1 * | 9/2004 | Nikolchev | 606/108 |
| 2004/0220609 A1 * | 11/2004 | Douk et al. | 606/200 |
| 2004/0225299 A1 * | 11/2004 | Carrison et al. | 606/108 |

FOREIGN PATENT DOCUMENTS

| | | |
|---|---|---|
| WO | WO 02/096273 A2 | 12/2002 |
| WO | WO 03/051444 A1 | 6/2003 |

OTHER PUBLICATIONS

U.S. Appl. No. 10/745,911, filed Dec. 23, 2003 by Wallace et al.

* cited by examiner

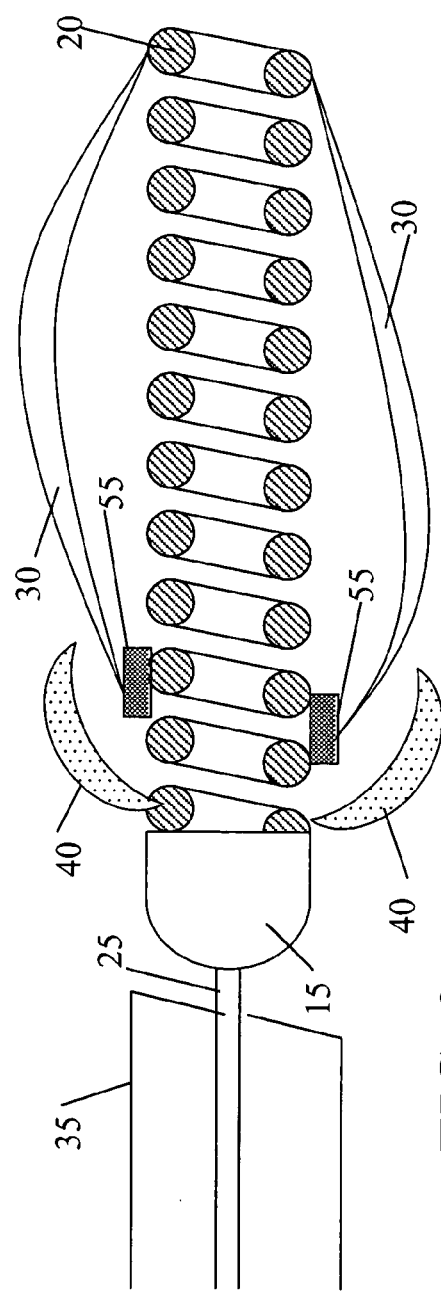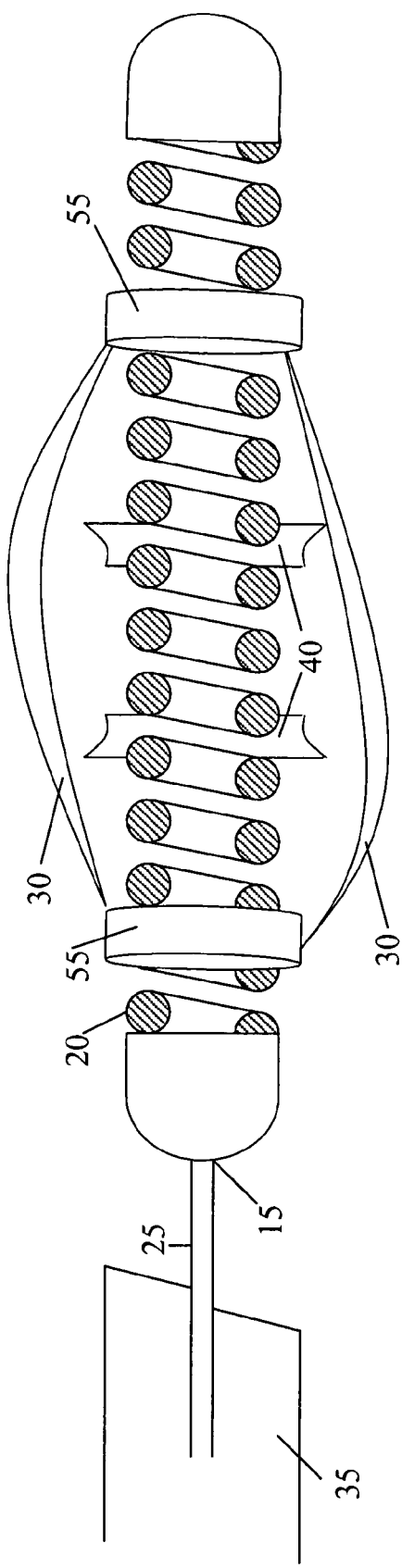
FIG. 3
FIG. 4

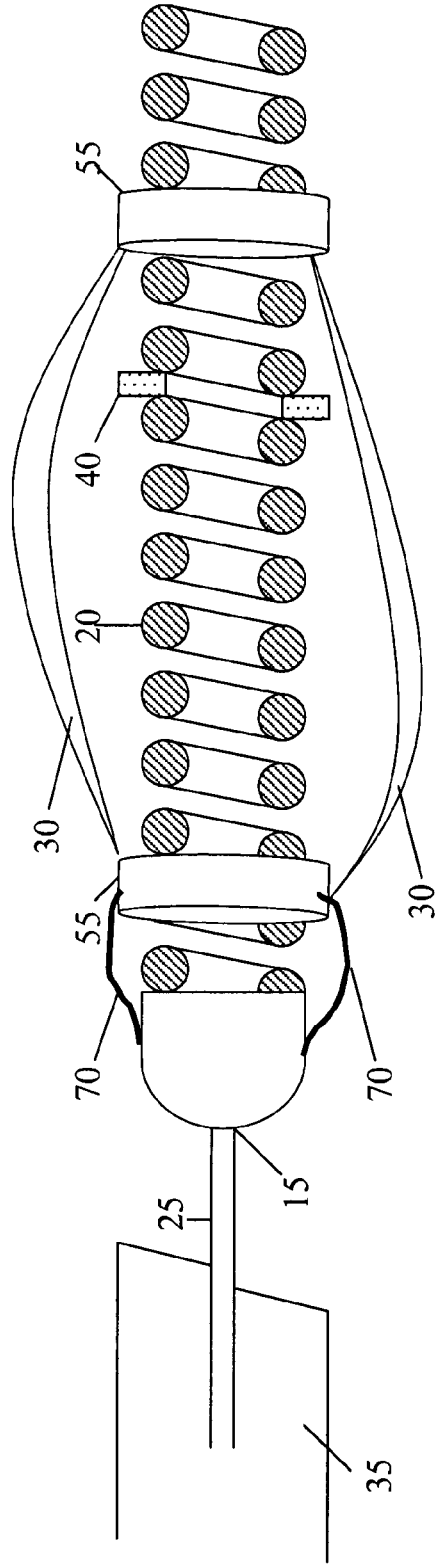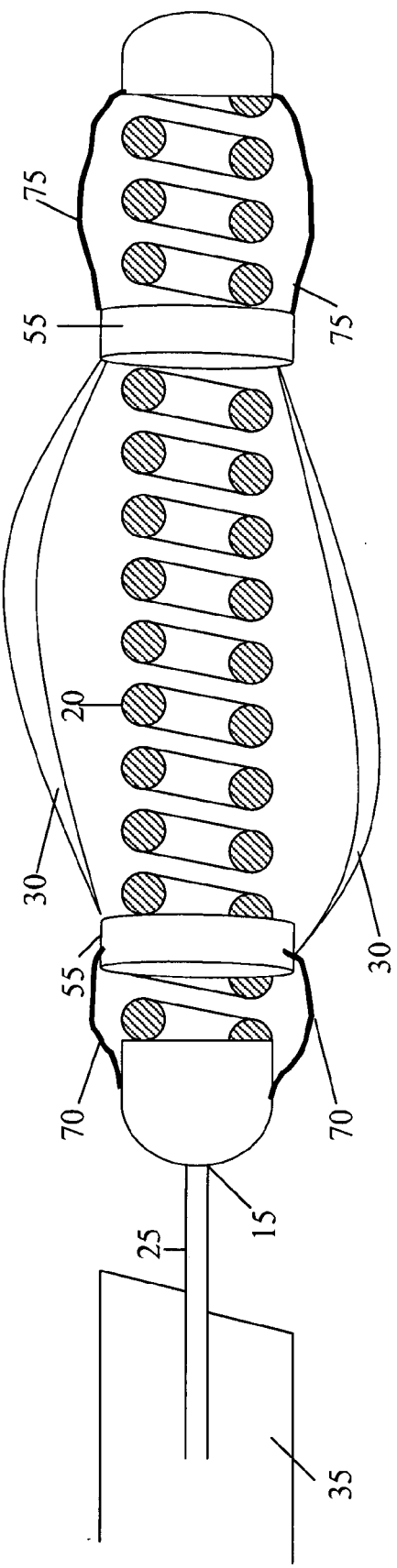

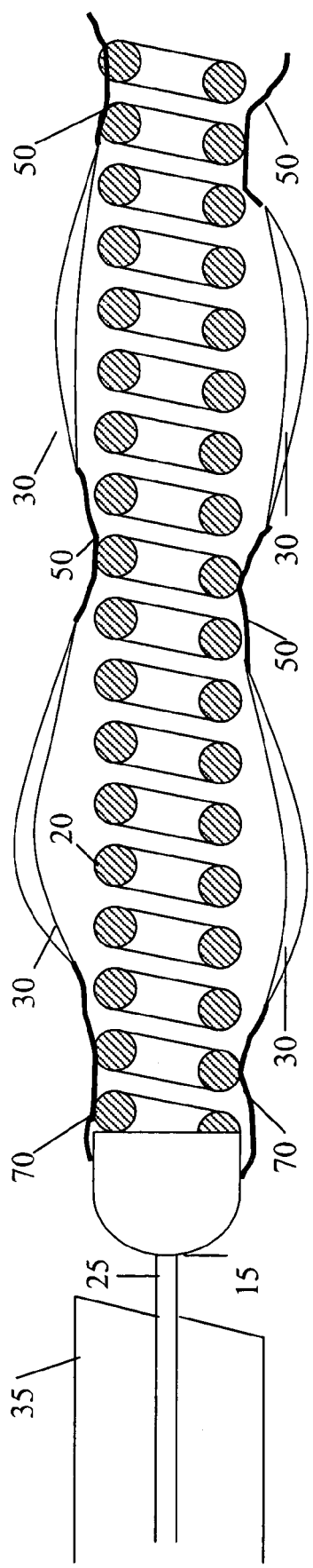
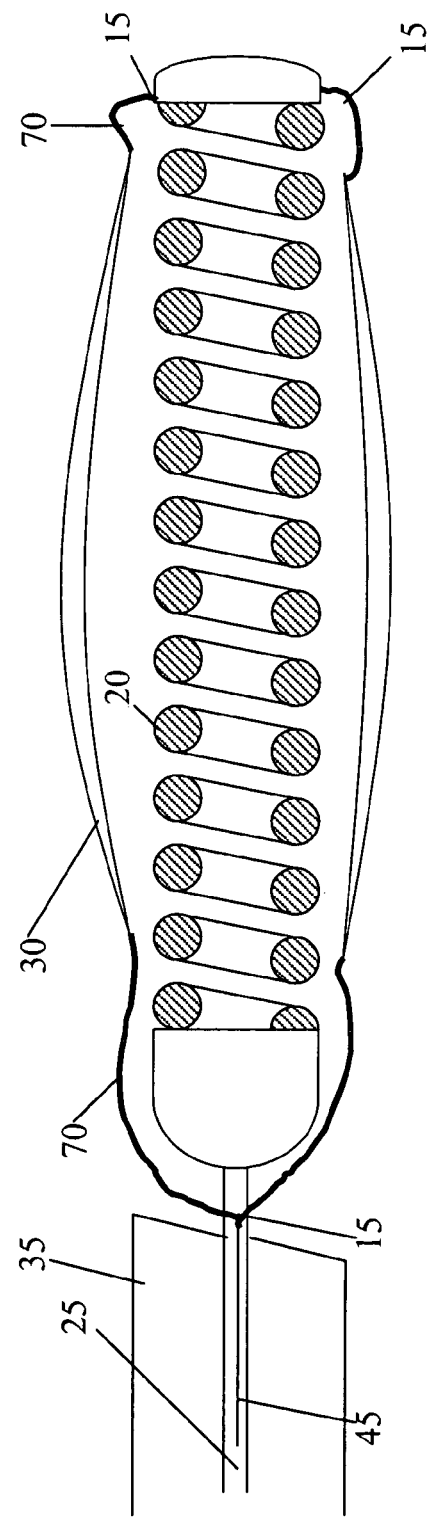
FIG. 8
FIG. 9

EXPANDING VASO-OCCLUSIVE DEVICE

FIELD OF THE INVENTION

Compositions and methods for repair of aneurysms are described. In particular, vaso-occlusive devices are disclosed, as are methods of making and using these devices.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. (See, e.g., U.S. Pat. No. 4,994,069 to Ritchart et al.) Other less stiff helically coiled devices have been described, as well as those involving woven braids. See, e.g., U.S. Pat. No. 6,299,627.

U.S. Pat. No. 5,354,295 and its parent, U.S. Pat. No. 5,122,136, both to Guglielmi et al., describe an electrolytically detachable embolic device. Vaso-occlusive coils having little or no inherent secondary shape have also been described. For instance, co-owned U.S. Pat. Nos. 5,690,666; 5,826,587; and 6,458,119 by Berenstein et al., describes coils having little or no shape after introduction into the vascular space. U.S. Pat. No. 5,382,259 describes non-expanding braids covering a primary coil structure.

U.S. patent application Ser. No. 10/745,911, filed Dec. 23, 2003 and incorporated herein by reference in its entirety, discloses embolic compositions comprising an expandable element that is free from hydrogels that expands along its primary axis upon deployment.

However, none of the above documents show a device as described herein including one or more stop elements that allow for ease of movement of the device during placement, re-positioning and/or retrieval.

SUMMARY OF THE INVENTION

Thus, this invention includes novel occlusive compositions as well as methods of using and making these compositions.

In certain aspects, the invention includes a vaso-occlusive device comprising an inner member having an axial length; a substantially tubular expandable member disposed around the inner member, wherein the expandable member slides along at least a portion of the axial length of the inner member; and a stop element attached to the inner member. The expandable member may comprise a braid configuration and the inner member may comprise a coil configuration. Furthermore, the expandable member and/or the inner member may comprise one or more metals (e.g., nickel, titanium, platinum, pallidum, rhodium, gold, tungsten, iridium and alloys or combinations thereof) or metal alloys (e.g., a stainless steel or super-elastic metal alloy such as nitinol). In certain embodiments, the stop element comprises a polymer.

Any of the devices described herein may further comprise a severable junction detachably which may be connected to a pusher element. The detachment junction can be positioned anywhere on the device, for example at one or both ends of the device. In certain embodiments, the severable junction(s) are, an electrolytically detachable assembly adapted to detach by imposition of a current; a mechanically detachable assembly adapted to detach by movement or pressure; a thermally detachable assembly adapted to detach by localized delivery of heat to the junction; a radiation detachable assembly adapted to detach by delivery of electromagnetic radiation to the junction or combinations thereof. The detachment junction(s) may be attached to inner member, expandable member and/or stop element.

Any of the devices described herein may further comprise one or more sliding elements disposed around the inner member. The expandable member is typically attached to the sliding element(s). In certain embodiments, the sliding element comprises polymer.

In any of the devices described herein, the expandable member may be attached to the inner member in at least one location.

Any of the devices (or individual components of the devices) described herein may further comprise one or more additional components, for example bioactive and/or biodegradable agents.

In another aspect, the invention includes a method of occluding a body cavity comprising introducing any of the vaso-occlusive devices described herein into a body cavity (e.g., an aneurysm).

These and other embodiments of the subject invention will readily occur to those of skill in the art in light of the disclosure herein.

BRIEF DESCRIPTION OF THE FIGURES

FIG. 3 depicts a side view cross-section of another exemplary assembly as described herein having a coil-shaped inner member and a braided expandable member attached at its proximal end to a sliding element. In this embodiment, the external stop element comprises a cuff-like structure surrounding the inner member and positioned proximal to the sliding element.

FIG. 4 depicts a side-view cross-section of another exemplary assembly as described herein having a coil-shaped inner member and a braided expandable member attached at both ends to sliding elements distinct from the expandable member. Two internal stop elements are depicted surrounding the inner member and positioned between the optionally distinct sliding members. Each stop element is depicted as a flared cuff-like structure.

FIG. 6 depicts a side-view cross-section of another exemplary assembly as described herein having a coil-shaped inner member and a braided expandable member. In this embodiment, the expandable member is attached to two sliding elements, one at the proximal end of the braid and one at the distal end of the braid. The proximal sliding element is also attached to the inner member by external string-like stop elements. Additional internal stop element(s) are positioned between the sliding elements.

FIG. 7 depicts a side-view, cross section of an exemplary device similar that depicted in FIG. 6. In the variation shown in FIG. 7, external stop elements in the form of strings (e.g., sutures) extend from the distinct distal sliding element to the distal end of the inner member.

FIG. 8 depicts a side-view, cross-section of another exemplary device including multiple expandable segments and multiple external stop elements.

FIG. 9 depicts a side-view, cross-section of another variation in which the external stop elements are detachable from the inner member such that upon deployment, the inner member can be removed and the expandable member left in the target site.

DESCRIPTION OF THE INVENTION

Occlusive (e.g., embolic) compositions are described. The compositions described herein find use in vascular and neurovascular indications and are particularly useful in treating aneurysms, for example small-diameter, curved or otherwise difficult to access vasculature, for example aneurysms, such as cerebral aneurysms. Methods of making and using these vaso-occlusive elements also form aspects of this invention.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to a device comprising "a stop element" includes devices comprising of two or more elements.

The device is a surgical implement and can be readily deployed, removed and/or repositioned in human vasculature. It is also suitably flexible to be placed in the distal tortuous vasculature of the brain.

Typically, the devices include an inner member (which may be removeable), one or more expandable members and one or more stop elements. The expandable member is capable of sliding along at least a portion of the length of the inner member. The sliding element may be distinct from the expandable member or may be integral to the expandable member, for example, by ensuring that selected portions of the expandable member slide in relation to the inner member.

Depicted in the Figures are exemplary embodiments of the present invention in which the inner member is depicted as a coil and the expandable member is depicted as a braided element. It will be appreciated that this is for purposes of illustration only and that the expandable member and/or inner member can be of other materials or shapes, for example as described in U.S. patent application Ser. No. 10/745,911, incorporated by reference in its entirety herein.

Figure 1:
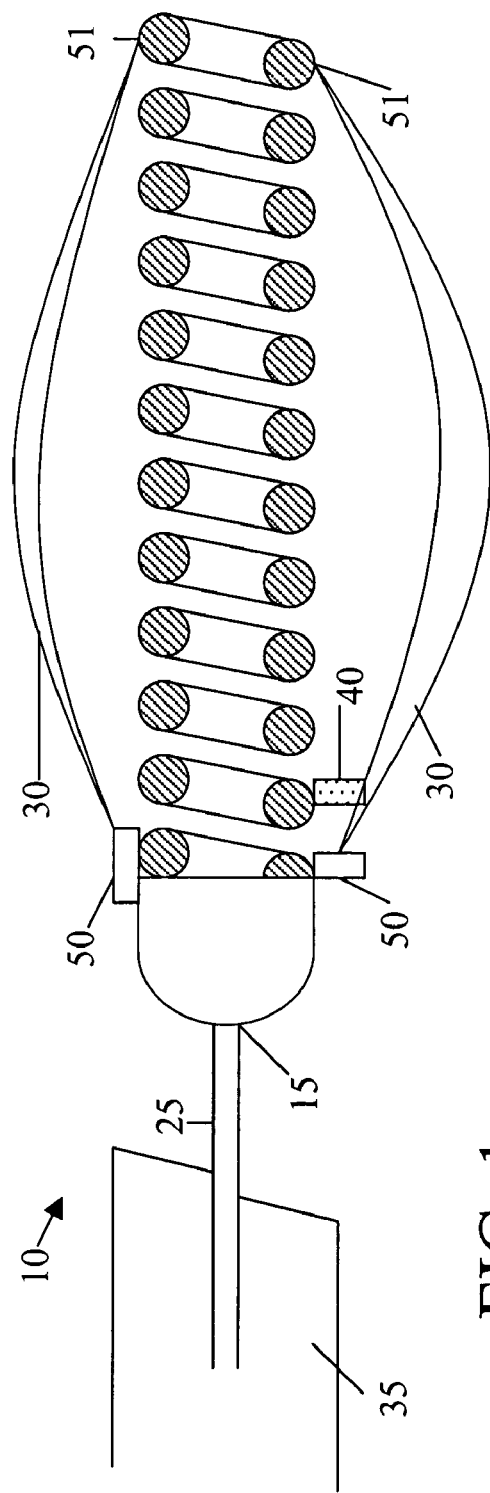
FIG. 1 depicts a side-view cross-section of an exemplary assembly as described herein having a coil-shaped inner member and a braided expandable member. The proximal end of the expandable member is slideably attached to the inner member. An internal stop element is shown attached to the inner member near the sliding portion of the expandable member.

FIG. 1 depicts an exemplary embodiment of the inventive vaso-occlusive devices described herein. The device as a whole is generally designated (10). Also shown are detachment junction (15), pusher wire (25), deployment device (e.g., catheter) (35), inner member (20), expandable member (30) and stop element (40). Stop element (40) is internal to the expandable member (30), is bonded to inner member (20) and does not move. The diameter of stop element (40) is such that it engages the expandable member (30) as the device (10) is moved through deployment catheter (35) and thereby limits bunching and overexpansion of the expandable element in the catheter (35). As discussed below, stop element(s) may be positioned at any suitable location, so long as they serve this function. In the embodiment shown in FIG. 1, the stop element (40) is positioned near the proximal sliding portion (50) of the expandable member (30).

As shown in FIG. 1, sliding element (50) is integral to (e.g., formed from) the expandable member (30). Integral sliding element (50) slides in an axial direction along the inner member (20) near the distal and proximal ends of the inner member (20). The distal end of the expandable member is also attached (51), either fixedly or slideable, to the coil. It will be readily apparent that the expandable member can be made slideable in relation to the inner member by a variety of ways, including, for example, cinching of the expandable members to form slideable portions. Further, the expandable member (30) can be permanently or temporarily attached to the inner member by any suitable attachment mechanism.

Figure 2:
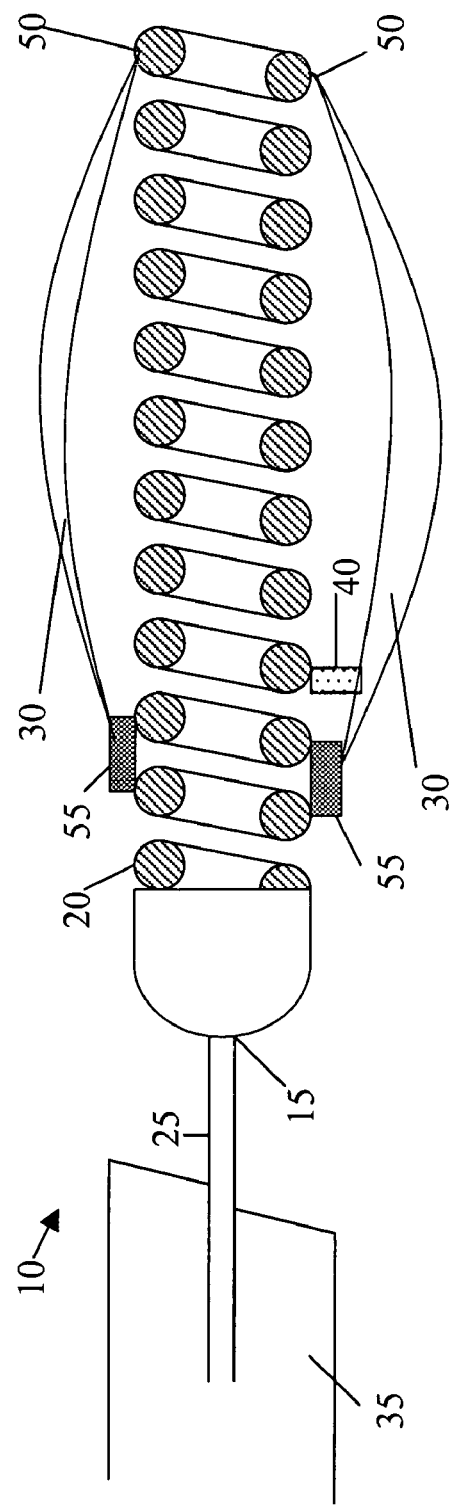
FIG. 2 depicts a side-view cross-section of an exemplary assembly as described herein having a coil-shaped inner member, a braided expandable member and an internal stop element. In this embodiment, the expandable member is attached at its proximal end to a distinct sliding element and is slideably attached at its distal end directly to the inner member. The distinct sliding element is positioned proximal to stop element.

FIG. 2 shows an exemplary embodiment that includes an expandable member (30) having a distinct sliding element (55) at is proximal end. Distinct sliding element (55) is disposed around the inner member (20) and attached to the expandable member (30). At its distal end, the expandable member may be fixedly or slideably attached (50) to the coil. Distinct sliding element (55) can only slide distally until it reaches the internal stop element (40). Thus, stop element (40) serves to prevent the expandable member (30) from over-expanding during delivery and/or retrieval.

FIG. 3 shows another variation including a cuff-shaped external stop element (40) attached to the proximal end of the inner member (20) and proximal to distinct sliding element (55). Expandable member (30) is also attached to the distal end of the inner member (20), either via direct attachment to the inner member or via an intermediate element. When present, the intermediary element may be fixedly attached to the inner member (20) or may be removable from the inner member (20), for example an additional sliding element.

FIG. 4 shows another embodiment having two internal stop elements (40) positioned between two sliding elements (50). In this embodiment, stop elements (40) have a flared cuff-like configuration, with the flared side facing the sliding element (50). In this variation, expandable member (30) is attached to distinct sliding elements (55) disposed around inner member.

Figure 5:
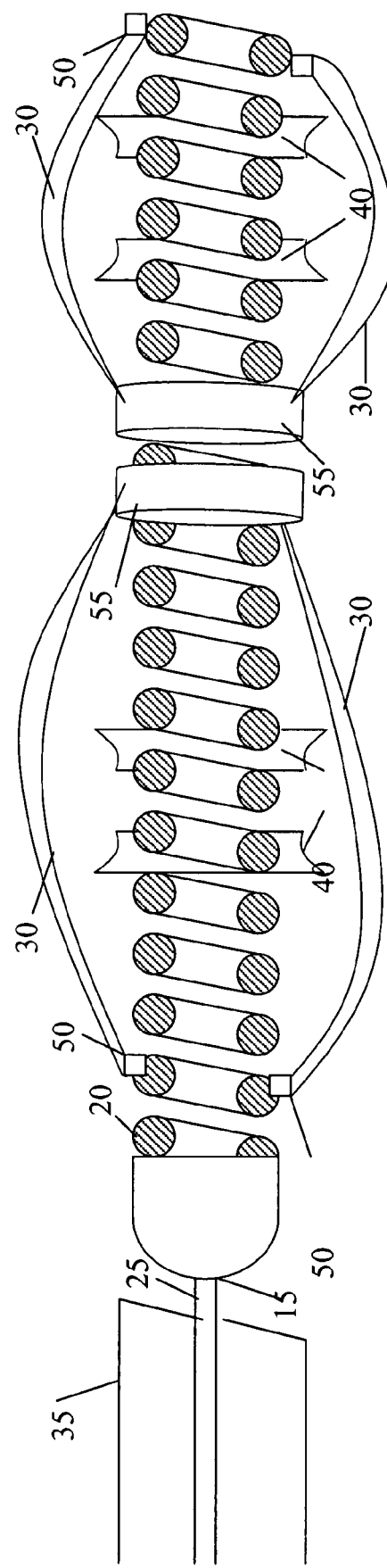
FIG. 5 depicts a side-view cross-section of another exemplary assembly as described herein having a coil-shaped inner member and a plurality of braided expandable members. Each expandable member is attached at its proximal end to a distinct sliding element and at its distal end to another distinct sliding element. The distinct sliding elements surround the inner member. This variation comprises a plurality of internal stop elements, each comprising a flared cuff-like structure surrounding the inner member and positioned between the sliding elements of each expandable member.

FIG. 5 shows another embodiment including multiple expandable members (30), multiple stop elements (40), multiple integral sliding elements (50) and multiple distinct sliding elements (55). Each expandable member (30) is attached at its proximal end to a sliding element (50, 55) and at its distal end to another sliding element (50, 55). Two flared cuff-like stop elements (40) are fixed to the inner member (20) and are positioned between the proximal and distal ends of each pair of sliding elements (50, 55). Inner member (20) can slide with respect to both expandable members (30).

FIG. 6 shows another variation including internal (40) and external (70) stop elements. Expandable member (30) is attached to distinct sliding elements (55). Internal stop element (40) is fixed to the inner member (20) and is positioned proximal and near to the distal sliding member (55) when the expandable member (30). External stop elements (70) are attached to the proximal sliding element (55) and to proximal end of inner member (20). External stop elements (70) can be any material, for example a suture that is slack when the assembly is moved in one axial direction and engages the expandable member with the inner member when the assembly is moved in the other axial direction.

FIG. 7 shows another variation in which multiple external stop elements (70) are used in conjunction with multiple distinct sliding elements (55).

FIG. 8 shows another variation including multiple segments of expandable members (30), integral sliding elements (50) and external stop elements (70).

FIG. 9 shows yet another embodiment in which detachment junctions (15) are included on external stop elements (70). In this variation, the inner member can be removed after the expandable member (30) has been deployed. Removing the inner member creates a lumen into which it may be possible to add larger volumes of additional (e.g., bioactive components), for example to the inside of the expandable member (30). In addition, expansion of the expandable member (30) may be more complete in the absence of an inner member (20).

Thus, a variety of embodiments can be used to the devices described herein allow for the efficient deployment of expandable devices into any target vessel.

Figure 12:
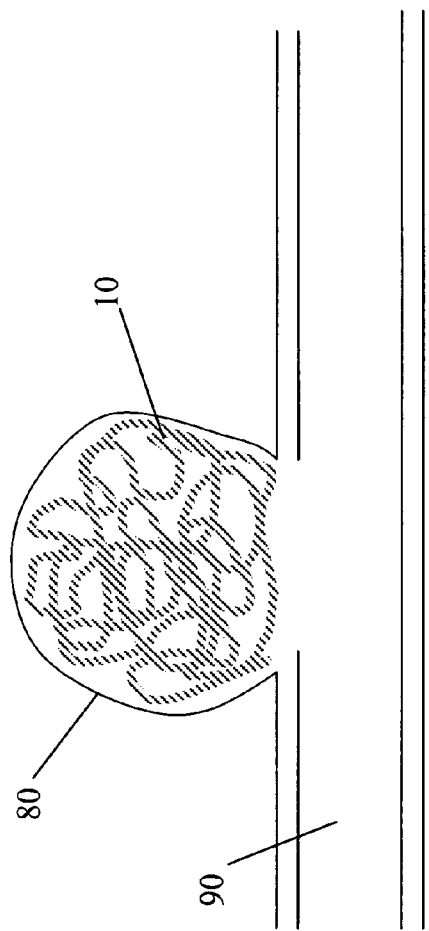
FIG. 12 depicts an exemplary device (10) as described herein as deployed within an aneurysm (80).

The expandable member may assume a variety of structures including, but not limited to, braids, coil, stents (e.g., self-expanding stents) and combinations of these. By "expandable," is meant that the element increases in diameter along its primary axis. See, also, U.S. patent application Ser. No. 10/745,911. The overall structure of the expandable member is preferably tubular, although as shown in the drawings, the diameter of this element is not necessarily constant along its length. Furthermore, in addition to expanding along its primary axis upon deployment, the overall three-dimensional configuration of the expandable member typically changes change upon deployment from the pre-deployment linear, tubular configuration. For example, the expandable member may form a coil configuration or may have a substantially random space-filling relaxed configuration (FIG. 12) upon deployment.

With regard to materials, it is to be understood that the expandable member may be made of a variety of materials, including but not limited to metals, polymers and combinations thereof. See, e.g., U.S. Pat. Nos. 6,585,754 and 6,280,457 for a description of various polymers. In certain embodiments, the expandable member is a braided structure comprising one or more metals or metal alloys, for example, Platinum Group metals, especially platinum, rhodium, palladium, rhenium, as well as tungsten, gold, silver, tantalum, stainless steel and alloys of these metals. Preferably, the expandable member comprises a material that maintains its shape despite being subjected to high stress, for example, "super-elastic alloys" such as nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol." The expandable member may also comprise a shape memory polymer such as those described in International Publication WO 03/51444. Preferably, the expandable member is free of any hydrogels (substances that are gels in an aqueous environment and expand to at least 10 times their original size upon contact with water), but may include one or more non-hydrogel polymers that do expand.

Like the expandable member, the inner member may assume a variety of structure and be comprised of a variety of materials. Thus, although depicted in the Figures as a coil (e.g., platinum coil), the inner member may be of a variety of shapes or configuration including, but not limited to, braids, wires, knits, woven structures, tubes (e.g., perforated or slotted tubes), injection-molded devices and the like. See, e.g., U.S. Pat. No. 6,533,801 and International Patent Publication WO 02/096273. The inner member may be made of any of the materials described above, for example, metals (e.g., platinum group metals described above), metal alloys, polymers or combinations of these materials. In addition, the inner member may be coated with one or more biodegradable and/or bioactive coatings, for example as described in U.S. Pat. No. 6,280,457. In certain embodiments, the inner member is a platinum coil. The inner member may also change shape upon release from the restraining member, for example change from a constrained linear form to a relaxed, three-dimensional configuration upon deployment. However, the inner member does not expand along its primary axis in the sense of the expandable member.

As noted above and shown in the Figures, the expandable member slides along a portion of the inner member. The sliding elements may be integral to the expandable member (e.g., portions of the expandable member can be made to slide in relation to the inner member) and/or may be distinct from the expandable member. Integral sliding elements can be made in a variety of ways including, for example, by cinching the expandable member to a diameter slightly larger than the inner and/or by bonding/attaching the expandable member to a piece of polymeric tubing such as Teflon™ that is typically of a diameter slightly larger than the inner member. Distinct sliding element(s) are typically disposed around the inner member (20). Combinations of integral and distinct sliding elements can be used in one device.

Integral and/or distinct sliding element(s) can be made of any number of materials, for example metals and polymers described above including but not limited to, stainless steel, platinum, kevlar, PET, carbothane, cyanoacrylate, epoxy, poly(ethyleneterephthalate) (PET), polytetrafluoroethylene (Teflon™), polypropylene, polyethylene, polyglycolic acid, polylactic acid, nylon, polyester, fluoropolymer, and copolymers or combinations thereof.

An important feature of the devices described herein is the inclusion of one or more stop elements that limit the expansion of the expandable member in the delivery mechanism (e.g., delivery catheter). Generally, the stop elements function to engage the expandable member with the inner member (e.g., at the proximal and/or distal ends), thereby keeping the diameter of the expandable member constrained within the deployment device. Thus, stop element(s) are positioned anywhere on the device that serves limit the expansion of the expandable member during deployment, re-positioning and/or retrieval.

Stop elements can be external and/or internal to the expandable member. Both external and internal stop elements are generally fixedly attached to the inner member in at least one location, although in certain embodiments, they may be detachable.

Exemplary internal stop elements include bumper-like shape (FIG. 2), flared cuff-like shapes (e.g., FIGS. 4, 5) and the like. It will be apparent that the internal stop elements can take other shapes, for example, rounded structures, bumps, etc. Whatever shape of the stop element, it may be fixed or may be capable of assuming an open, flared configuration, for example when engaged by sliding of the expandable member along the inner member. Other configurations such as prongs, hooks (both fixed or expandable when engaged) and the like can also employed for internal stop elements.

Figure 10:
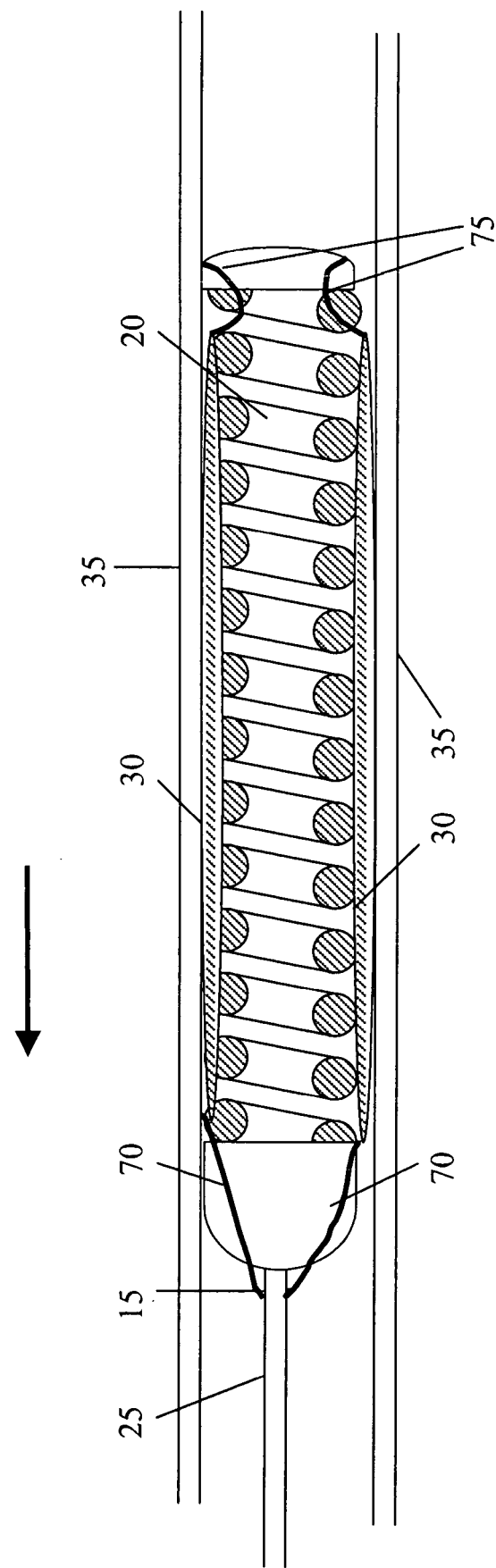
FIG. 10 depicts a side-view, cross-section of the embodiment shown in FIG. 9 within a delivery catheter. The dark arrow shows the direction of movement. When the device is pulled back through the catheter as shown, the external proximal stop elements are taut and the distal stop elements are slack.

Exemplary external stop elements include cuff-like structures (FIG. 3) and string like structures (FIGS. 6 to 8) such as wires, strings, sutures and/or other suitable string-like materials. External stop elements may also take the form of prongs, hooks and the like. External stop element(s) are preferably bonded to the inner member (20) or may be detachable from the inner member (20) and/or pusher wire (25) (FIGS. 9, 10).

Stop elements of similar or different configurations (e.g., external and/or internal) can be used in the same device. For instance, FIG. 6 shows a device including a bumper type stop element as well as a string type stop element. Stop elements (internal and/or external) can be made any material, for example, metals and polymers described above including but not limited to, stainless steel, platinum, kevlar, PET, carbothane, cyanoacrylate, epoxy, poly(ethyleneterephthalate) (PET), polypropylene, polyethylene, polyglycolic acid, polylactic acid, nylon, polyester, fluoropolymer, and copolymers or combinations thereof.

Pusher wire (25) or other elements may be made of, or coated with, a material such as polytetrafluoroethylene (e.g., Teflon™) and desirably extends all the way to the proximal end of the catheter. The pusher wire (25) may be rotatable and axially moveable with respect to the device. Pusher wire (25) can also act as a guidewire and may be used to provide a pathway through tortuous vasculature for the device to follow.

Any of the devices described herein may further comprise a detachment junction (15), which is severable. The detachment junction (15) may be connected to a pusher element, such as a pusher wire. The detachment junction can be positioned anywhere on the device, for example at one or both ends of the device.

In certain embodiments, the inner member may be removed after deployment. As shown in FIG. 9, the detachment junctions (15) are positioned so that only the expandable member is detached from the assembly and the inner member can be withdrawn. The detachment junction (15) may be the pusher wire (25) itself. Alternatively, as depicted in FIG. 9, detachment may be from a separate element (45), for example a conductive wire element suitable for electrolytic detachment. The wire is typically insulated until the detachment junction (15). In this embodiment, pusher wire (25) is typically a metal and polymer composite.

The severable junction(s) may be detached in a variety of ways, for example using an electrolytically detachable assembly adapted to detach by imposition of a current; a mechanically detachable assembly adapted to detach by movement or pressure; a thermally detachable assembly adapted to detach by localized delivery of heat to the junction; a radiation detachable assembly adapted to detach by delivery of electromagnetic radiation to the junction or combinations thereof. Furthermore, the detachment mechanism may be hydraulic, for example the pusher wire may be cannulated, for example to allow for saline injection through the pusher wire to push off the coil.

The devices described herein may also comprise additional components, such as co-solvents, plasticizers, coalescing solvents, bioactive agents, antimicrobial agents, antithrombogenic agents (e.g., heparin), antibiotics, pigments, radiopacifiers and/or ion conductors which may be coated using any suitable method or may be incorporated into the element(s) during production. See, e.g., co-owned U.S. patent application Ser. No. 10/745,911, U.S. Pat. No. 6,585,754 and WO 02/051460, incorporated by reference in their entireties herein. The bioactive materials can be coated onto the device (e.g., heparin) and/or can be placed in the vessel prior to, concurrently or after placement of one or more devices as described herein. For example, in embodiments in which the inner member is removed after deployment of the expandable member, one or more bioactive materials can be delivered to the lumen of the expandable member.

As noted elsewhere, the location of the device is preferably visible using fluoroscopy. A highly preferred method is to ensure that at least some of the elements (e.g., expandable member and/or inner member) making up the device are provided with significant radio-visibility via the placement of a radio-opaque covering on these elements. A metallic coating of a metal having comparatively more visibility, during fluoroscopic use, than stainless steel is preferred. Such metals are well known but include gold and members of the Platinum Group described above.

One of more of the elements may also be secured to each other at one or more locations. For example, to the extent that various elements are thermoplastic, they may be melted or fused to other elements of the devices. Alternatively, they may be glued or otherwise fastened. Furthermore, the various elements may be secured to each other in one or more locations.

Methods of Use

The embolic compositions described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, occlusive devices (and/or additional components) described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g. vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the vaso-occlusive device at the distal end, is advanced through the catheter.

Once the selected site has been reached, the vaso-occlusive device is extruded, for example by loading onto a pusher wire. Preferably, the vaso-occlusive device is loaded onto the pusher wire via a mechanically or electrolytically cleavable junction (e.g., a GDC-type junction that can be severed by application of heat, electrolysis, electrodynamic activation or other means). Additionally, the vaso-occlusive device can be designed to include multiple detachment points, as described in co-owned U.S. Pat. Nos. 6,623,493 and 6,533,801 and International Patent publication WO 02/45596. They are held in place by gravity, shape, size, volume, magnetic field or combinations thereof.

Figure 11:
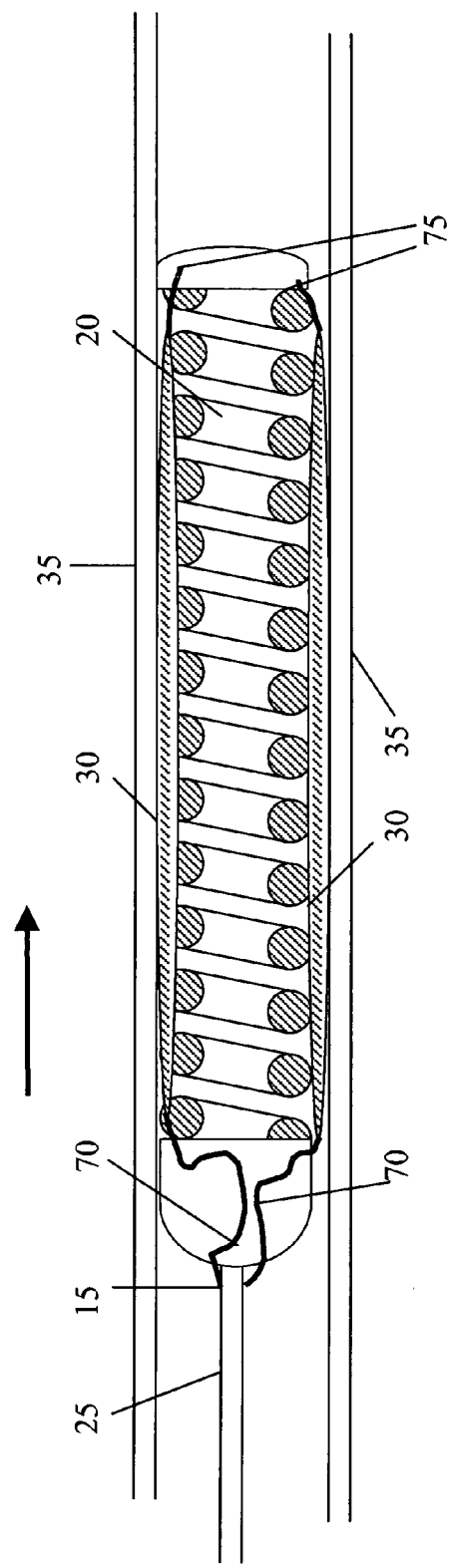
FIG. 11 depicts a side-view, cross-section of the embodiment shown in FIG. 9 within a delivery catheter. The dark arrow shows the direction of movement. When the device is pushed through the catheter as shown, the external distal stop elements are taut and the proximal stop elements are slack.

During deployment, it is possible that friction may be created when the device is moved through the deployment mechanism (e.g., catheter), for example by the force exerted by the linearly constrained expandable member on the walls of the catheter. As noted above, the devices described herein include one or more stop elements that may limit bunching and expansion of the expandable member during deployment. As depicted in FIGS. 10 and 11, the stop elements (70, 75) keep the expandable member (30) taut as it is pushed through the delivery catheter (35). This reduced friction against the walls of the delivery catheter and eases delivery. FIG. 10 shows a device as described herein as it is pulled back through a deliver catheter (35). The dark arrow shows the direction of motion. As the device is pulled back, the proximal stop elements (70) are taut while the distal stop elements (75) are slack. FIG. 11 shows a device as described herein as it is pushed out of a delivery catheter. As the device is pushed, distal stop elements (75) are taut while proximal stop elements (70) are slack. Thus, in either axial direction, the stop elements cause the expandable member (30) to engage the inner member (20) and assume a lower profile (smaller diameter) that makes movement through the catheter (35) easier.

As noted above with regard to FIG. 9, it will also be apparent that in certain embodiments, the inner member (20) is removeable after deployment into the vessel. For example, the device can be deployed into a vessel (aneurysm) as described herein. Once deployed, the expandable member (30) is detached from the inner member (20) while the inner member (20) remains attached to the pusher wire (25) and can be removed from the vessel.

It will also be apparent that the operator can remove or reposition (distally or proximally) the expandable member. For instance, the operator may choose to insert a device as described herein, before detachment, move the pusher wire to place the device in the desired location.

Modifications of the procedure and vaso-occlusive devices described above, and the methods of using them in keeping with this invention will be apparent to those having skill in this mechanical and surgical art. These variations are intended to be within the scope of the claims that follow.

What is claimed is:

1. A method of occluding an aneurysm comprising introducing a vaso-occlusive device into the aneurysm such that the vaso-occlusive device assumes its relaxed, three-dimensional configuration within the aneurysm, thereby occluding the aneurysm, the vaso-occlusive device comprising:
   an implantable vaso-occlusive device having a linear configuration within a restraining member and a relaxed, three-dimensional configuration upon release from the restraining member, the linear configuration of the device comprising
   an inner member having an axial length:
   a substantially tubular expandable member disposed around the inner member, wherein the expandable member slides along at least a portion of the axial length of the inner member;
   a stop element attached to the inner member; and
   a detachment junction;
   and wherein the relaxed, three-dimensional configuration of the implanted vaso-occlusive device is adapted to be placed within an aneurysm such that the device occludes the aneurysm.

2. The method of claim 1, wherein the stop element comprises a polymer.

3. The method of claim 1, wherein the expandable member comprises a braid configuration.

4. The method of claim 1, wherein the inner member comprises a coil.

5. The method of claim 1, wherein the expandable member comprises a metal.

6. The method of claim 5, wherein the metal is selected from the group consisting of nickel, titanium, platinum, gold, tungsten, iridium and alloys or combinations thereof.

7. The method of claim 6, wherein the metal is nitinol or platinum.

8. The method of claim 1, wherein the inner member comprises a coil comprising a metal selected from the group consisting of platinum, palladium, rhodium, gold, tungsten and alloys thereof.

9. The method of claim 1, wherein the inner member comprises a coil comprising a stainless steel or super-elastic metal alloy.

10. The method of claim 4, wherein the coil member comprises nitinol.

11. The method of claim 1, wherein the detachment junction comprises an electrolytically detachable end adapted to detach from a pusher by imposition of a current on the pusher.

12. The method of claim 1, wherein the detachment junction is attached to the inner member.

13. The method of claim 1, wherein the detachment junction is attached to the stop element.

14. The method according to claim 1, further comprising a sliding element disposed around the inner member, wherein the expandable member is attached to the sliding element.

15. The method of claim 14, wherein the sliding element comprises a polymer.

16. The method of claim 1, wherein the expandable member is attached to the inner member in at least one location.

17. The method of claim 1, further comprising an additional component.

18. The method of claim 17, wherein the additional component is bioactive.

* * * * *